US011429900B1

(12) United States Patent
Alvarenga Marinelli

(10) Patent No.: US 11,429,900 B1
(45) Date of Patent: Aug. 30, 2022

(54) SYSTEMS AND METHODS FOR AUTOMATIC DETECTION OF ERROR CONDITIONS IN MECHANICAL MACHINES

(71) Applicant: Tractian Limited, Grand Cayman (KY)

(72) Inventor: Igor Vinicius Alvarenga Marinelli, São Paulo (BR)

(73) Assignee: Tractian Limited, Grand Cayman (KY)

( * ) Notice: Subject to any disclaimer, the term of this patent is extended or adjusted under 35 U.S.C. 154(b) by 0 days.

(21) Appl. No.: 17/511,539

(22) Filed: Oct. 26, 2021

(51) Int. Cl.
| | | |
|---|---|---|
| *G05B 13/02* | (2006.01) | |
| *G06N 20/00* | (2019.01) | |
| *G05B 19/418* | (2006.01) | |
| *H04R 3/00* | (2006.01) | |
| *G01N 29/11* | (2006.01) | |
| *G05B 19/4065* | (2006.01) | |
| *G01N 29/50* | (2006.01) | |
| *A61B 5/316* | (2021.01) | |
| *G06N 3/04* | (2006.01) | |

(Continued)

(52) U.S. Cl.
CPC ............ *G06N 20/00* (2019.01); *G01N 29/11* (2013.01); *G01N 29/50* (2013.01); *G05B 19/4065* (2013.01); *G05B 19/4183* (2013.01); *G05B 19/4184* (2013.01); *G05B 19/41885* (2013.01); *H04R 3/005* (2013.01); *A61B 5/316* (2021.01); *G01B 9/02027* (2013.01); *G01H 1/003* (2013.01); *G06N 3/0454* (2013.01)

(58) Field of Classification Search
CPC .... G01N 29/50; G01N 29/11; G05B 19/4065; G05B 19/4183; G05B 19/4184; G05B 19/41885; G01H 1/003; A61B 5/316; H04R 3/005; H04R 25/507; G06N 3/0454; G06N 20/00; C21D 10/00; G01B 9/02027; G06F 11/079
See application file for complete search history.

(56) References Cited

U.S. PATENT DOCUMENTS

| | | | | |
|---|---|---|---|---|
| 4,823,599 A | * | 4/1989 | Schneider | .............. C21D 10/00 73/579 |
| 5,895,857 A | * | 4/1999 | Robinson | ............... G01N 29/11 73/660 |

(Continued)

*Primary Examiner* — Tuan A Vu
(74) *Attorney, Agent, or Firm* — Cognition IP, P.C.; Edward Steakley; Rajesh Fotedar

(57) ABSTRACT

A sensor device is coupled to a mechanical machine. The sensor device detects vibrations of the mechanical machine and transmits the vibration data to a remote processing device. The vibration data may be compressed prior to transmission. The remote processing device receives the data and generates a reconstructed version of the vibration data. The remote processing device includes a machine learning model trained to examine vibration data and to identify a motion pattern associated with an error condition. The machine learning model is applied to the reconstructed vibration data and detects an occurrence of an error condition in the mechanical machine. An alert indicating that an error condition has been detected is transmitted to a human operator. The human operator verifies the status of the mechanical machine and confirms that an error condition has occurred. In response to receipt of the confirmation, the machine learning model is further trained on training data updated to include the vibration data generated by the mechanical machine.

10 Claims, 16 Drawing Sheets

(51) Int. Cl.
*G01B 9/02015* (2022.01)
*G01H 1/00* (2006.01)

(56) References Cited

U.S. PATENT DOCUMENTS

| | | | | |
|---|---|---|---|---|
| 6,549,869 | B1* | 4/2003 | Piety | G01H 1/003 |
| | | | | 340/635 |
| 7,379,846 | B1* | 5/2008 | Williams | G06F 11/079 |
| | | | | 702/183 |
| 8,174,402 | B2* | 5/2012 | Bouse | G05B 19/4065 |
| | | | | 340/679 |
| 10,997,970 | B1* | 5/2021 | Rafii | H04R 25/507 |
| 2012/0013909 | A1* | 1/2012 | Podoleanu | G01B 9/02027 |
| | | | | 356/451 |
| 2012/0197153 | A1* | 8/2012 | Kraus | A61B 5/316 |
| | | | | 600/545 |
| 2018/0011065 | A1* | 1/2018 | Bowers, III | G01N 29/50 |
| 2019/0122689 | A1* | 4/2019 | Jain | H04R 3/005 |
| 2021/0057084 | A1* | 2/2021 | Takeshima | G06N 3/0454 |

\* cited by examiner

| Machine Type | Machine Power | Machine Category | Vel RMS | Vel MAD | Accel RMS | Accel MAD | Vel Crest Factor | Accel Crest Factor | TAG |
|---|---|---|---|---|---|---|---|---|---|
| Centrifugal Pump | 15KW | 1F | 1.35 | 1.12 | 0.12 | 0.24 | 2.8 | 2.78 | Unbalance |
| Reciprocating Pump | 78KW | 4S | 0.98 | 1 | 0.64 | 1.54 | 21.12 | 32.1 | Misalignment |
| Electric Motor | 0.5KW | 1S | XXX | XXX | XXX | XXX | XXX | XXX | Looseness |
| XXX | XXX | XXX | XXX | XXX | XXX | XXX | XXX | XXX | Bearings |

SYSTEMS AND METHODS FOR AUTOMATIC DETECTION OF ERROR CONDITIONS IN MECHANICAL MACHINES

TECHNICAL FIELD

This specification relates generally to methods of operating and maintaining machinery, and more particularly to systems and methods for detecting an error condition in a mechanical machine.

BACKGROUND

A mechanical machine is any machine, generally rotating, that performs mechanical work. This mechanical work results from a transformation of received energy, which may be electrical, thermal or mechanical. Machines such as electric motors, hydraulic pumps, compressors, fans, generators and turbines are examples of mechanical machines.

It is well known that mechanical machines occasionally experience mechanical problems i.e., error conditions such as wear, corrosion, obstructions, blockages, misalignments, unbalances, structural or rotating looseness, and other issues that may cause a failure or a risk condition. In a commercial facility housing multiple mechanical machines, frequent mechanical problems can be costly, requiring significant time and money to monitor and repair.

In many existing facilities, machines must be monitored by an experienced human operator, and each mechanical issue is diagnosed and repaired manually. However, a mechanical problem is often undetectable in its early stages and therefore cannot be identified by a human operator until it has developed into a more significant (and more costly) problem. For example, a mechanical issue may begin as a misalignment that is undetectable to a human operator. If the misalignment goes undetected, the error condition may develop into a more serious issue and may even cause damage to the mechanical machine. Therefore, in a facility (e.g., an industrial facility) with a large number of mechanical machines, the risk associated with mechanical failures can be substantial. In order to address this risk, in many facilities a significant amount of labor is spent manually monitoring the mechanical machines. However, even human experts often fail to identify mechanical problems sufficiently early to avoid costly repairs. Accordingly, there is an ongoing need for improved systems and methods to detect problems that occur in mechanical machines.

SUMMARY

Systems and methods for detecting an error condition in a mechanical machine are disclosed. In accordance with an embodiment, a sensor device is coupled to a mechanical machine. The sensor device detects vibrations of the mechanical machine and transmits the vibration data to a remote processing device. The vibration data may be compressed prior to transmission. The remote processing device receives the data and generates a reconstructed version of the vibration data. The remote processing device includes a machine learning model trained to examine vibration data and to identify a motion pattern associated with an error condition. The machine learning model is applied to the vibration data and detects an occurrence of an error condition in the mechanical machine. An alert indicating that an error condition has been detected is transmitted to a human operator. The human operator verifies the status of the mechanical machine and confirms that an error condition has occurred. In response to receipt of the confirmation, the machine learning model is further trained on training data updated to include the vibration data generated by the mechanical machine.

In accordance with another embodiment, vibration data representing vibrations generated by a mechanical machine is obtained by a first device. A frequency representation of the vibration data is generated in a frequency spectrum by the first device. The frequency representation includes a plurality of points defined by respective coefficients. For each of the plurality of points in the frequency representation, a modulus of a magnitude and phase of the respective point is determined by the first device, in order to generate modulus data. A predetermined number of peaks in the frequency representation are selected by the first device, based on the modulus data. Peaks information representing the selected number of peaks is transmitted by the first device to a second device. Reconstructed vibration data representing the vibration data is generated by the second device based on the peaks information. A pattern within the reconstructed vibration data indicating an error condition experienced by the mechanical machine is identified by the second device.

In one embodiment, the first device includes a sensor and is disposed on the mechanical machine.

In another embodiment, the mechanical machine is a compressor, a motor, a turbine, a pump, a bearing, a reductor, a fan, or a gearbox.

In another embodiment, a modified Discrete Fourier Transform, using Fast Fourier Transform, is used to generate a frequency representation of the vibration data.

In another embodiment, one hundred (100) peaks in the frequency representation are selected by the first device, based on the modulus data.

In another embodiment, the error condition includes a blockage, a cavitation, corrosion, an imbalance, a lubrication, a resonance, a rotating looseness, a deposit, a structural looseness, an operator error, or a transmitted fault.

In another embodiment, a pattern is identified, by the second device, within the reconstructed vibration data indicating an error condition experienced by the mechanical machine, by training a machine learning model on stored data that includes a plurality of samples of vibration data associated with one or more mechanical machines, and applying the machine learning model to the reconstructed vibration data.

In another embodiment, the pattern indicating an error condition is identified by the machine learning model. A human operator is alerted that the pattern has been identified. A confirmation is received from the human operator that the error condition exists. The pattern is added to the stored data, in response to receiving the confirmation from the human operator.

In accordance with another embodiment, a system includes a first device having a sensor, a processor, and a transmitting device. The sensor is adapted to obtain vibration data representing vibrations generated by a mechanical machine. The processor is adapted to generate a frequency representation of the vibration data in a frequency spectrum, wherein the frequency representation includes a plurality of points defined by respective coefficients, determine, for each of the plurality of points in the frequency representation, a modulus of a magnitude and phase of the respective point, to generate modulus data, and select a predetermined number of peaks in the frequency representation based on the modulus data. The transmitting device is adapted to transmit, to a second device, peaks information representing the selected number of peaks. The second device is adapted to generate, based on the peaks information, reconstructed vibration data representing the vibration data, and identify a pattern within the reconstructed vibration data indicating an error condition experienced by the mechanical machine.

In accordance with another embodiment, a sensor device includes a sensor, a processor, and a transmitting device. The sensor is adapted to obtain vibration data representing vibrations generated by a mechanical machine. The processor is adapted to apply a modified Discrete Fourier Transform, using Fast Fourier Transform, to generate a frequency representation of the vibration data in a frequency spectrum, wherein the frequency representation includes a plurality of points defined by respective coefficients, determine, for each of the plurality of points in the frequency representation, a modulus of a magnitude and phase of the respective point, to generate modulus data, and select a predetermined number of peaks in the frequency representation based on the modulus data. The transmitting device is adapted to transmit, to a second device, peaks information representing the selected number of peaks.

These and other advantages of the present disclosure will be apparent to those of ordinary skill in the art by reference to the following Detailed Description and the accompanying drawings.

BRIEF DESCRIPTION OF THE DRAWINGS

FIG. 12 shows a table that contains exemplary characteristics associated with various types of machines in accordance with an embodiment.

DETAILED DESCRIPTION

In accordance with an embodiment, a sensor device is coupled to a mechanical machine. The sensor device detects vibrations of the mechanical machine and transmits the vibration data to a remote processing device. The vibration data may be compressed prior to transmission. The remote processing device receives the data and, if necessary, generates a reconstructed version of the vibration data. The remote processing device includes a machine learning model trained to examine vibration data and to identify a motion pattern associated with an error condition. The machine learning model is applied to the vibration data and detects an occurrence of an error condition in the mechanical machine. An alert indicating that an error condition has been detected is transmitted to a human operator. The human operator verifies the status of the mechanical machine and confirms that an error condition has occurred. In response to receipt of the confirmation, the machine learning model is further trained on training data updated to include the vibration data generated by the mechanical machine.

The term "vibration" is used herein to refer to the motion of a mechanical machine when the device is in operation. Similarly, the term "vibration data" is used to refer to data representing the motion of a mechanical machine when the device is in operation. However, use of this language is not to be construed as limiting, and it is to be understood that systems, apparatus and methods described herein are applicable to any type of motion associated with mechanical machines.

Figure 1:
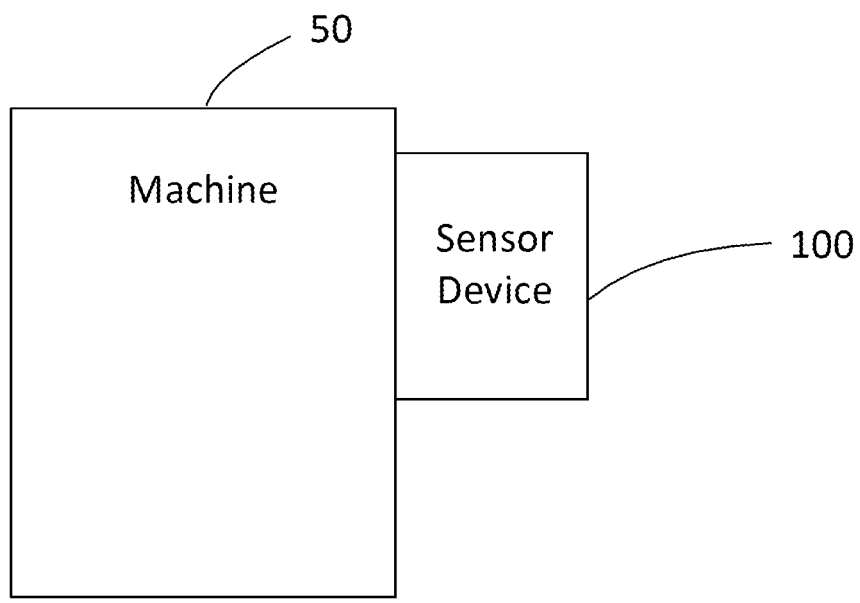
FIG. 1 shows a machine and a sensor device coupled to the machine in accordance with an embodiment.

FIG. 1 shows a mechanical machine (sometimes referred to herein as a machine) and a sensor device coupled to the machine in accordance with an embodiment. Machine 50 may be any type of mechanical machine. In the illustrative embodiment, machine 50 is a compressor. In other embodiments, machine 50 may be a different type of mechanical machine such as (without limitation) a motor, a turbine, pump, bearing, reductor, fan, gearbox, etc.

In one embodiment, sensor device 100 is attached to an external surface of machine 50. In other embodiments, sensor device 100 may be disposed on an internal surface of machine 50, or may be attached to a selected part within machine 50.

Figure 2:
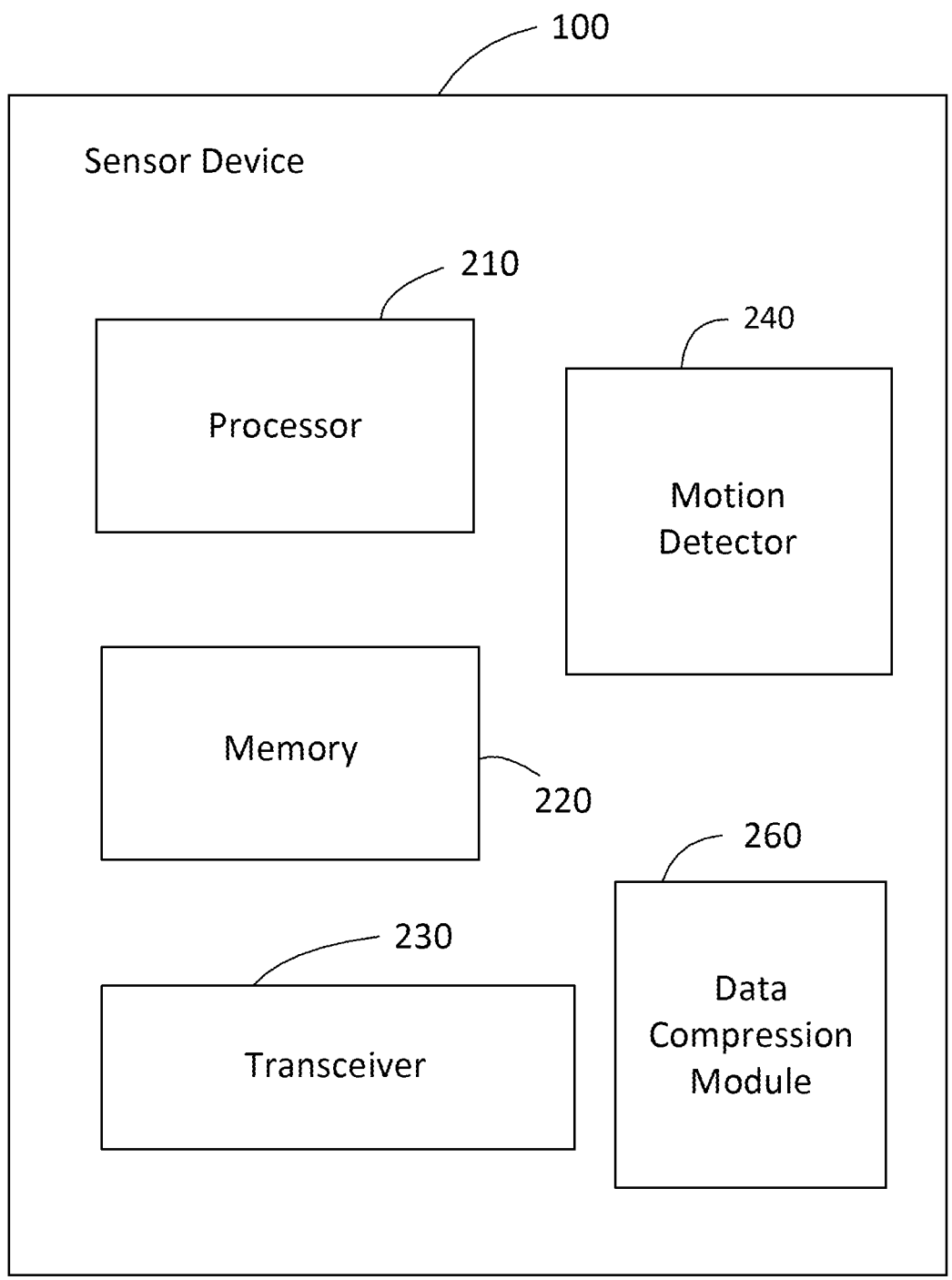
FIG. 2 shows components of sensor device in accordance with an embodiment.

FIG. 2 shows components of sensor device 100 in accordance with an embodiment. Sensor device 100 includes a processor 210, a memory 220, a transceiver 230, a motion detector 240, and a data compression module 260. Processor 210 controls the operation of other components of sensor device 100. Memory 220 is adapted to store data. For example, processor 210 or motion detector 240 may from time to time store data in memory 220. Transceiver 230 is adapted to transmit and receive data. Thus, transceiver 230 may function as a transmitting device adapted to transmit data and/or as a receiving device adapted to receive data. In one embodiment, transceiver 230 transmits and receives data wirelessly. Transceiver 230 may include one or more antennae, for example. Motion detector 240 is adapted to detect and measure motion. For example, motion detector 240 may detect and measure any movements of sensor device 100. Motion detector 240 may measure motion in three dimensions (for example, along predefined x, y, and z axes, or along horizontal and vertical axes and axially). Data compression module 260 is adapted to compress data generated by motion detector 240 into a form optimized for transmission via a network to a second device. Data compression module 260 may use one or more algorithms to compress data.

Many mechanical machines vibrate when in operation. A particular mechanical machine may vibrate with a characteristic frequency when operating in a particular mode. If the mechanical machine experiences a mechanical issue, such as a misalignment, it may vibrate with a different frequency or cease to vibrate entirely. Motion detector 240 detects motion in multiple dimensions and therefore may measure the vibrations of machine 50 while the machine is operating.

In one embodiment, motion detector 240 detects and measures the vibrations of machine 50 and transmits data representing the vibrations to processor 210. For example, the vibrations of machine 50 may be transferred to sensor device 100 because sensor device 100 is physically coupled to machine 50. Processor 210 causes data compression module 260 to compress the vibration data, and processor 210 causes transceiver 230 to transmit the compressed vibration data wirelessly to a remote device. Processor 210 may also store the vibration data in memory 220.

In accordance with an embodiment, machine 50 is a piece of industrial machinery, for example, a machine in a manufacturing facility, a power generation facility, a distribution center, etc. Sensor device 100 is attached to machine 50. Consequently, when machine 50 vibrates while in operation, sensor device 100 generates vibration data representing the vibrations of machine 50.

In accordance with an embodiment, sensor device 100 samples relevant conditions (including vibrations) periodically and with a defined frame and frequency. The sample may include information relating to vibrations along three axes. For example, vibration data may include vibration data in x, y, and z axes, or in horizontal and vertical planes and axial motion.

In one embodiment, data compression module 260 converts the vibration data from the time domain to the frequency domain, generating spectrum data. Data compression module 260 may further compress the spectrum data, generating compressed spectrum data optimized for transmission via a communication network. Sensor device 100 may transmit the compressed spectrum data to a remote device for analysis.

Figure 3:
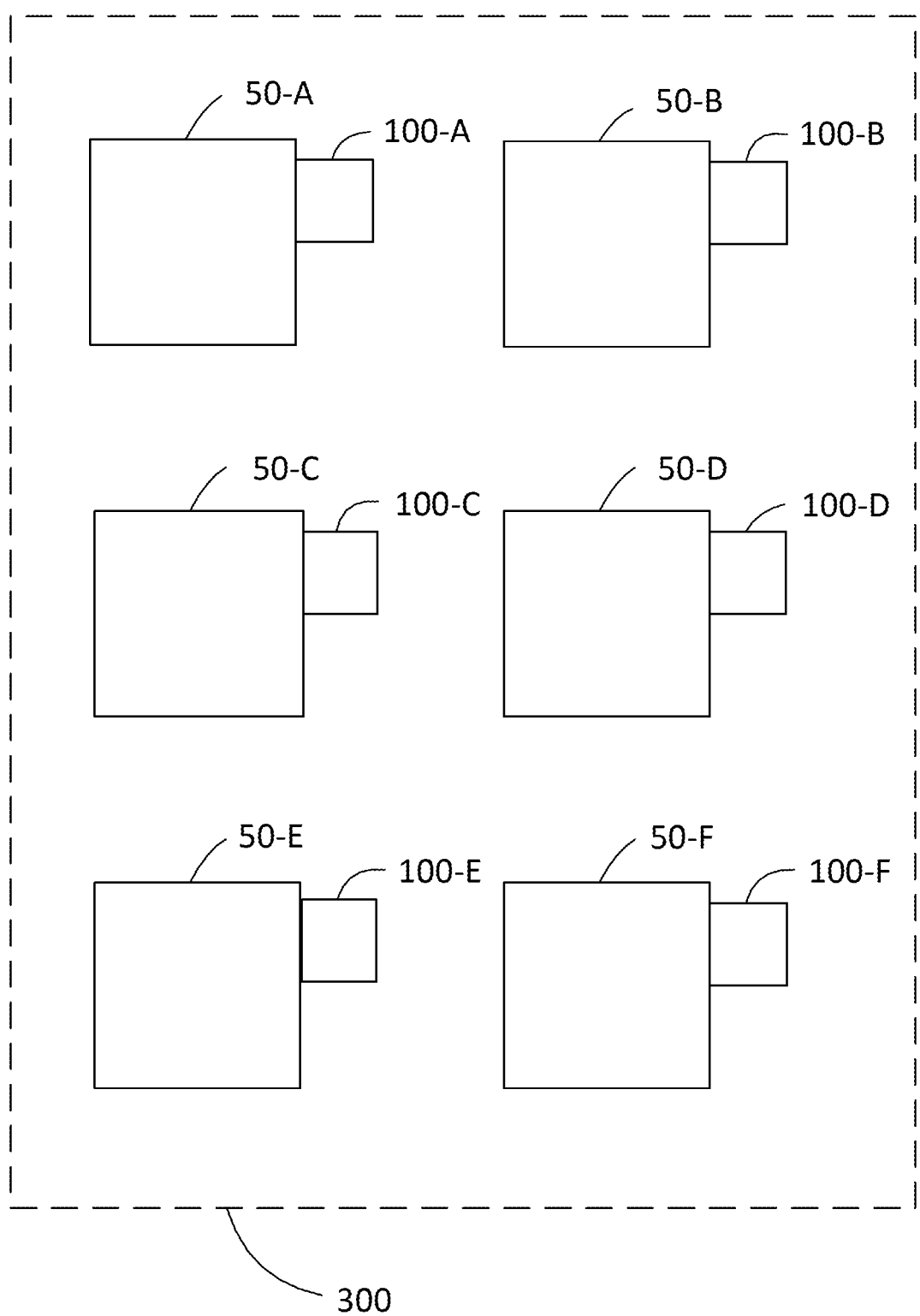
FIG. 3 shows a plurality of sensor devices attached to a plurality of machines in a facility in accordance with an embodiment.

In accordance with another embodiment, a plurality of sensor devices similar to sensor device 100 are attached to a plurality of machines in a facility. FIG. 3 shows a plurality of sensor devices attached to a plurality of machines in an industrial facility in accordance with an embodiment. Specifically, a facility 300 includes machines 50-A, 50-B, 50-C, 50-D, 50-E, and 50-F. Facility 300 may be a factory, a power plant, or other type of industrial facility housing a plurality of machines.

A plurality of sensor devices are attached to the machines. Specifically, sensor device 100-A is attached to machine 50-A, sensor device 100-B is attached to machine 50-B, sensor device 100-C is attached to machine 50-C, sensor device 100-D is attached to machine 50-D, sensor device 100-E is attached to machine 50-E, and sensor device 100-F is attached to machine 50-F. Sensor devices 100-A, 100-B, 100-C, 100-D, 100-E, and 100-F are sensor devices similar to sensor device 100 shown in FIG. 2. While six machines and six sensor devices are shown in FIG. 3, in other embodiments, more or fewer machines, and more or fewer sensor devices may be used.

Figure 4:
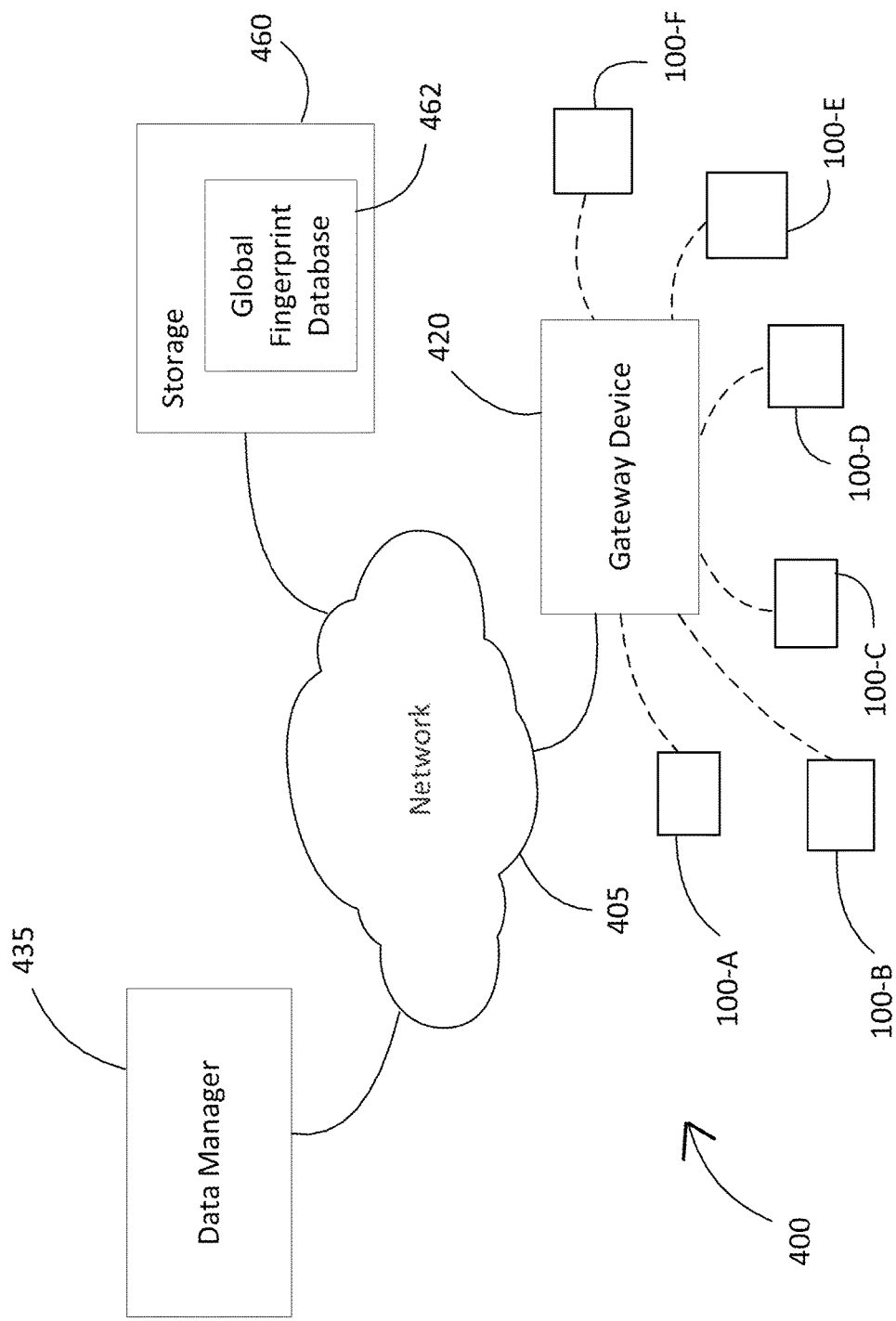
FIG. 4 shows a communication network in accordance with an embodiment.

In accordance with an embodiment, sensor devices 100 function as part of a communication network. FIG. 4 shows a communication network in accordance with an embodiment. Communication network 400 includes a network 405, a data manager 435, a storage 460, a gateway device 420, and sensor devices 100-A, 100-B, 100-C, 100-D, 100-E, and 100-F. Other types of communications networks, and other network configurations, may be used.

Network 405 may include an Internet, an Ethernet, a local area network (LAN), a wide area network (WAN), a wireless network, an optical network, or another type of network.

Each sensor device 100 obtains measurements related to the vibrations of a respective machine 50 (as illustrated in FIG. 3) and transmits vibration data to data manager 435 via gateway device 420 and network 405. For example, each sensor device 100 may transmit vibration data wirelessly to gateway device 420, which transmits the vibration data to data manager 435 via network 405. The vibration data may be processed and compressed prior to transmission.

Gateway device 420 includes a wireless modem (not shown). Gateway device 420 from time to time receives data from sensor devices 100-A, 100-B, 100-C, 100-D, 100-E, and 100-F. Gateway device 420 may from time to time store data, such as measurement data received from sensor devices 100, in storage 460.

Data manager 435 includes a processing device adapted to receive from sensor devices 100 measurement data relating to the vibrations of various machines and analyze the vibration data associated with each machine. Data manager 435 may be a server computer, a personal computer, a laptop device, a tablet device, a cellphone, etc. Other processing devices may be used.

Storage 460 is a storage device or system adapted to store data. Storage 460 may include one or more magnetic disks, internal hard disks and removable disks, magneto-optical disks, optical disks, etc. Storage 460 may include a cloud storage system.

Figure 5:
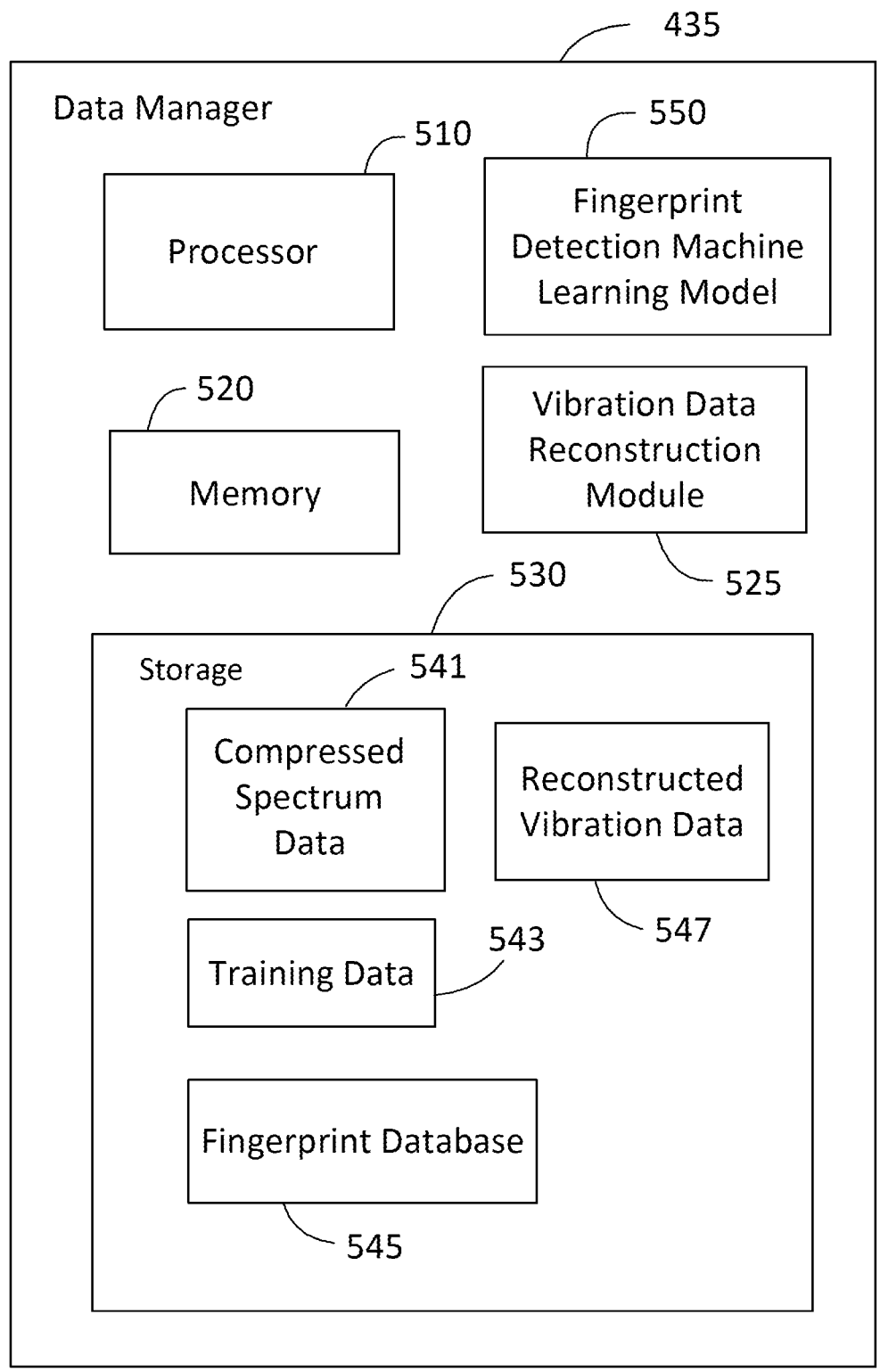
FIG. 5 shows components of a data manager in accordance with an embodiment.

FIG. 5 shows components of data manager 435 in accordance with an embodiment. Data manager 435 includes a processor 510, a memory 520, a vibration data reconstruction module 525, a storage 530, and a fingerprint detection machine learning model 550.

Processor 510 controls the operation of various components of data manager 435. Memory 520 is adapted to store data. For example, processor 510 and fingerprint detection machine learning model 550 may from time to time store data in memory 520.

Storage 530 is adapted to store data. For example, processor 510 and fingerprint detection machine learning model 550 may from time to time store data in storage 530.

Vibration data reconstruction module 525 is adapted to examine compressed spectrum data (representing vibrations generated by a mechanical machine) and reconstruct vibration data based on the compressed spectrum data.

From time to time data manager 435 receives, from a sensor device, compressed spectrum data representing vibrations of a particular machine. Processor 510 stores the compressed spectrum data in storage 530 as compressed spectrum data 541. Processor 510 instructs vibration data reconstruction module 525 to generate reconstructed vibration data based on the compressed spectrum data. The reconstructed vibration data is a reconstructed representation of the vibrations experienced by the machine. Processor 510 stores the reconstructed vibration data in storage 530 as reconstructed vibration data 547.

Fingerprint detection machine learning model 550 is trained to identify, classify, infer, and/or predict an occurrence of an error condition of a machine based on motion data associated with a machine. For example, fingerprint detection machine learning model 550 may detect within vibration data a pattern that is associated with a particular type of error condition. Such a pattern is referred to herein as a "fingerprint" or a "fingerprint signal."

Fingerprint detection machine learning model 550 is also trained to identify, classify, infer, and/or predict an occurrence of a pattern within vibration data that is associated with normal operation of a machine, i.e., a pattern that indicates that the machine is operating normally and is not experiencing an error condition. Such a pattern may also be referred to as a "fingerprint."

Any suitable type of machine learning model may be used, such as Mahalanobis distance, normality test, alarm values/tripvalues, decision tree (spectrum peaks), decision tree (harmonics), decision tree (unbalance, misalignment, looseness), Gaussian Mixture models, Neural Network (1D-input conv.).

Any suitable machine learning training technique may be used, including, but not limited to, a neural net based algorithm, such as Artificial Neural Network, Deep Learning; a robust linear regression algorithm, such as Random Sample Consensus, Huber Regression, or Theil-Sen Estimator; a kernel based approach like a Support Vector Machine and Kernel Ridge Regression; a tree-based algorithm, such as Classification and Regression Tree, Random Forest, Extra Tree, Gradient Boost Machine, or Alternating Model Tree; Naïve Bayes Classifier; and others suitable machine learning algorithms.

In one embodiment, fingerprint detection machine learning model 550 is trained with a training sample of hundreds or thousands of samples of vibration data obtained from machines during operation. Preferably, the training data includes vibration data generated by machines of the same or a similar type as machine 50. The training data may be supplemented by data generated by one or more experienced human operators who analyze the vibration data and identify patterns in the vibration data that indicate or are associated with error conditions, and/or patterns associated with normal operation of a machine.

Accordingly, fingerprint detection machine learning model 550 may from time to time be applied to vibration data associated with a particular machine. Upon examining the vibration data, fingerprint detection machine learning model 550 may identify a fingerprint signal in the vibration data and, based on the fingerprint signal, predict the occurrence of an error condition in the machine.

Figure 6A:
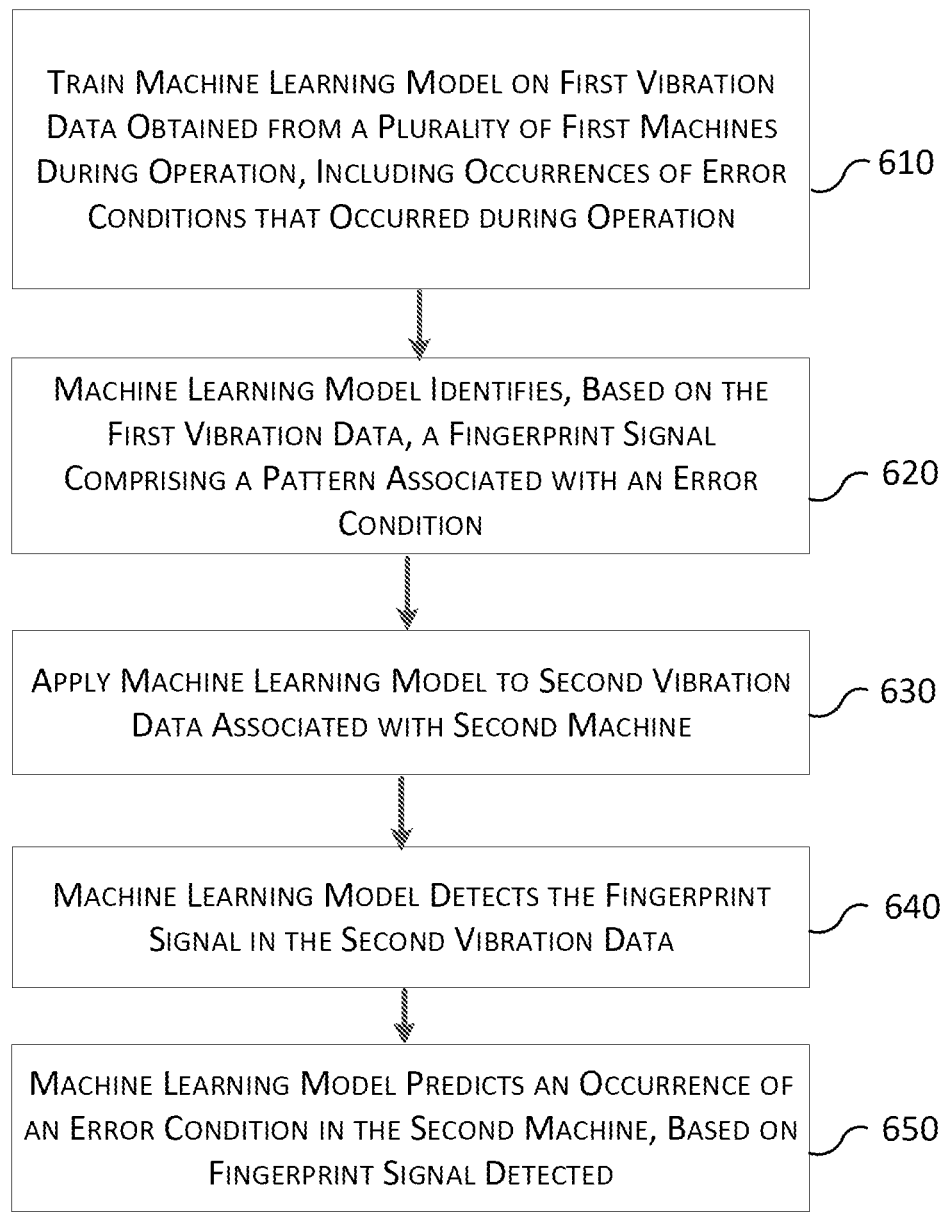
FIGS. 6A-6B include a flowchart of a method of detecting an occurrence of an error condition of a machine in accordance with an embodiment.
Figure 6B:
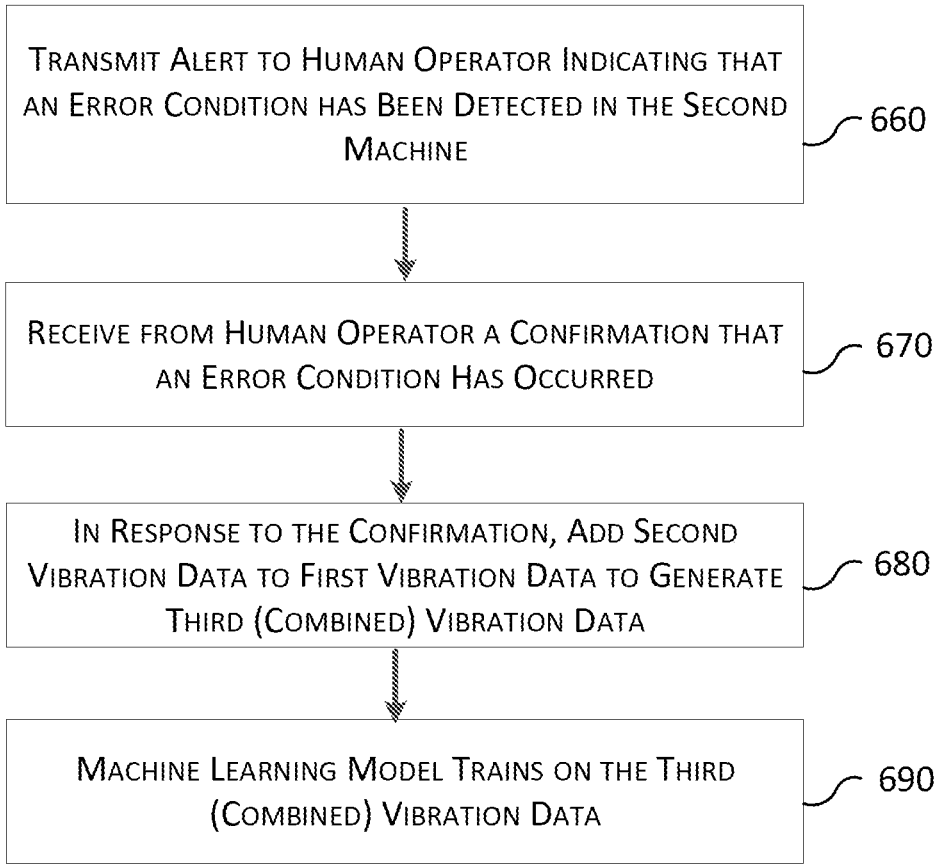

Thus, in an illustrative embodiment, data manager 435 receives from a sensor device compressed spectrum data associated with a mechanical machine, processes the compressed spectrum data to generate reconstructed vibration data, identifies a fingerprint signal in the reconstructed vibration data, and predicts an occurrence of an error condition in the mechanical machine based on the fingerprint signal. FIGS. 6A-6B include a flowchart of a method of identifying an occurrence of an error condition of a machine in accordance with an embodiment.

At step 610, a machine learning model is trained on first vibration data including data obtained from a plurality of first machines during operation, including occurrences of error conditions that occurred during operation. In the illustrative embodiment, as discussed above, fingerprint detection machine learning model 550 is trained with a training sample of hundreds or thousands of samples of vibration data obtained from machines during operation. In another embodiment, the machine learning model may be trained on vibration data obtained from a single machine in operation. The training data may be stored in storage 530. In the illustrative example, the training data is stored in storage 530 as training data 543.

An error condition in a machine may include any type of misalignment, malfunction, or other mechanical issue or problem. More specifically, an error condition may include, for example, and without limitation, failures such as: blockages, cavitations, corrosion, imbalance, lubrification, resonance, rotating looseness, deposits, structural looseness, operator error, transmitted fault, or an undetermined failure or error condition. Components that may experiences such conditions may include, without limitation, gears, rotors, bearings, rolling element bearings, journal bearings, flexible couplings, electrical parts, or an undetermined component.

In accordance with an embodiment, the training data includes one or more of the following types of information relating to samples of motion data: minimum values, maximum values, mean values, root mean square values, mean absolute deviation values, normality information, standard deviation values, covariance matrix, natural frequency values, fundamental frequency values, harmonic frequency values, skewness and Kurtosis information.

In accordance with an embodiment, the training data also includes one or more of the following types of information, which may be used to define the sampling behavior of the sensor device: frame length, sample interval, sensor sensitivity, vibration threshold, wake-up threshold, work days, work time, etc.

At step 620, the machine learning model identifies, based on the first vibration data, a fingerprint signal comprising a vibration pattern associated with an error condition. Fingerprint detection machine learning model 550 identifies a pattern in training data 543 associated with an error condition of a machine. When the machine learning model identifies, in the training data, a pattern (a fingerprint) associated with an error condition, information related to the fingerprint signal may be stored in storage 530. In the illustrative embodiment, information related to the fingerprint signal is stored in a fingerprint database 545 within storage 530.

In accordance with an embodiment, fingerprint detection machine learning model 550 may define a plurality of fingerprint signals, each associated with a respective type of error condition and with a respective machine component. Information relating to various fingerprint signals is stored in fingerprint database 545 within storage 530.

At step 630, the machine learning model is applied to second vibration data obtained from a second machine. For example, data manager 435 may receive from sensor device 100-A compressed spectrum data associated with machine 50-A. In the illustrative embodiment, processor 510 stores the compressed spectrum data associated with machine 50-A in storage 530 as compressed spectrum data 541.

Vibration data reconstruction module 525 generates reconstructed vibration data (representing vibrations experienced by machine 50-A) based on compressed spectrum data 541. The reconstructed vibration data is stored in storage 530, as reconstructed vibration data 547.

Processor 510 applies fingerprint detection machine learning model 550 to reconstructed vibration data 547.

In accordance with an embodiment, processor 510 may analyze the (reconstructed) vibration data received from sensor device 100-A, and generate additional, related data, which is added to the reconstructed vibration data. For example, processor 510 may generate the following values for both acceleration and velocity, based on the motion data: waveform root mean square (RMS) values (horizontal, vertical, and axial), waveform mean absolute deviation (MAD) values (horizontal, vertical, and axial), waveform envelope mean values (horizontal, vertical, and axial), waveform peak values (horizontal vertical, and axial), complete spectrum, and spectrum harmonics and peaks.

At step 640, the machine learning model detects the fingerprint signal in the second vibration data. Fingerprint detection machine learning model 550 is applied to reconstructed vibration data 547 (and any additional data provided by processor 510), and detects the fingerprint signal in the reconstructed vibration data.

At step 650, the machine learning model predicts an occurrence of an error condition in the second machine, based on the fingerprint signal detected. Thus, in response to detecting the fingerprint signal in reconstructed vibration data 547, fingerprint detection machine learning model 550 predicts an occurrence of an error condition in machine 50-A.

At step 660, an alert is transmitted to a human operator indicating that an error condition has been detected in the second machine. In the illustrative embodiment, processor 510 transmits a message to a human operator indicating that an error condition has been detected in machine 50-A. The message may specify the type of error condition that has been detected, and the component of the machine in which it has occurred. In the illustrative embodiment, the human operator may be, for example, an employee of facility 300 responsible for monitoring the status of machines 50.

In accordance with an embodiment, fingerprint detection machine learning model 550 generates two types of insights. When an insight is created it indicates that a possible failure of the machine, or risky situation relating to the machine, has been identified, and a human operator is alerted and asked to provide feedback relating to status of the machine. Generalist insights are alerts that are based on global values (RMS, MAD, peaks) and define limits taking into account distribution profiles. Specialist insights are alerts based on knowledge of mechanics, spectrum analysis and calibration of the machine learning model(s), which can distinguish faults such as unbalance, misalignment, mechanical play and bearing failures.

At step 670, a confirmation of the occurrence of an error condition is received from the human operator. In the illustrative embodiment, the human operator examines machine 50-A and determines that an error condition has occurred. Accordingly, the human operator provides to data manager 435 a confirmation that an error condition did occur in machine 50-A. Processor 510 receives and stores the confirmation message.

At step 680, in response to receipt of the confirmation from the human operator, the second vibration data is added to the first vibration data to generate third vibration data. In the illustrative embodiment, processor 510 updates training data 543 to include reconstructed vibration data 547. (If no confirmation is received from the human operator, then the second vibration data is not added to the first vibration data).

At step 690, the machine learning model is trained on the third vibration data. Fingerprint detection machine learning model 550 trains further on the updated training data 543. In this manner, fingerprint detection machine learning model 550 continually improves its ability to detect fingerprints associated with machine 50-A, and therefore improves its ability to detect error conditions that the machine may experience.

In various embodiments, sensor device 100 may include one or more of the following: a Triaxial 6.6 kHz MEMS Accelerometer to sample Vibration; a Temperature microelectromechanical system (MEM) sampling −30 to 90 degrees Celsius; a Microprocessor to store, extract, wake, sleep, analyze; a 4 MB Flash Memory to allow permanent storage of feedback parameters; a 2/3/4G Modem to transmit to a mobile carrier directly to cloud; one or more magnets for easy-to-use machine fixation; a ABS IP65 case adapted to provide protection in any harsh environment; and a 5 Volt Input or Battery plug.

In accordance with another embodiment, a sensor device obtains vibration data representing vibrations experienced by a mechanical machine, and generates a frequency representation of the vibration data in a frequency spectrum, wherein the frequency representation includes a plurality of points defined by respective coefficients. The sensor device determines, for each of a plurality of points in the frequency representation, a modulus of a magnitude and phase of the respective point, to generate modulus data, and selects N peaks in the frequency representation based on the modulus data. The sensor device transmits peaks information representing the N peaks to data manager 435. Data manager 435 generates reconstructed vibration data based on the peaks information, and identifies a pattern within the reconstructed vibration data indicating an error condition experienced by the mechanical machine.

Advantageously, systems and methods described herein enable transmission of information representing vibration data and reconstruction of the vibration data, the Phase and the Spectrum with less than one percent (1.0%) loss.

In the illustrative embodiment, sensor device 100 obtains vibration data representing vibrations generated by machine 50. Sensor device 100 generates a frequency representation of the vibration data, and generates a compressed data set including a selected portion of the frequency representation. Sensor device 100 transmits the compressed data set to data manager 435. Data manager 435 generates reconstructed vibration data based on the compressed data set. Data manager identifies a pattern in the reconstructed vibration data set that indicates an error condition experienced by machine 50.

Figure 7:
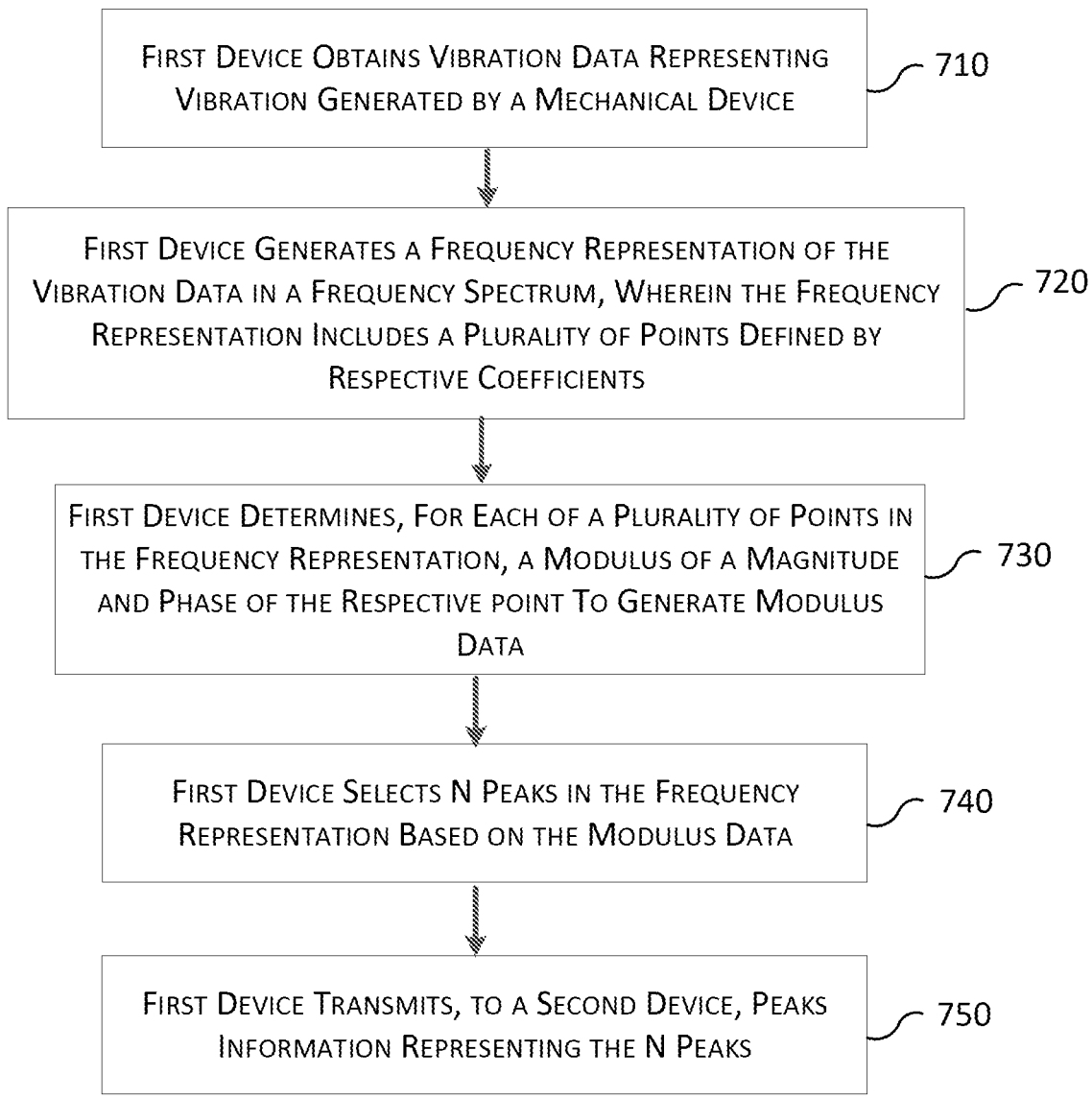
FIG. 7 is a flowchart of a method of obtaining, processing, and transmitting vibration data in accordance with an embodiment.

FIG. 7 is a flowchart of a method in accordance with an embodiment. At step 710, a first device obtains vibration data representing vibrations generated by a mechanical machine. In the illustrative embodiment, sensor device 100 obtains vibration data representing vibrations generated by machine 50. Sensor device 100 may store the vibration data, for example, in memory 220.

In one embodiment, sensor device 100 samples for about one second (4096 points in X axis, Y axis and Z axis) at 6,600 kHz range accelerometer.

At step 720, the first device generates a frequency representation of the vibration data in a frequency spectrum, wherein the frequency representation includes a plurality of points defined by respective coefficients. In the illustrative embodiment, data compression module 260 of sensor device 100 generates a frequency representation of the vibration data. Any suitable method may be used to generate a frequency representation. Data compression module 260 may store the frequency representation, for example, in memory 220.

At step 730, the first device determines, for each of a plurality of points in the frequency representation, a modulus of a magnitude and phase of the respective point, to generate modulus data. At step 740, the first device selects N peaks in the frequency representation based on the modulus data.

In the illustrative embodiment, data compression module 260 of sensor device 100 determines, for each of a plurality of points in the frequency representation, a modulus of a magnitude and phase of the respective point, to generate modulus data, and selects N peaks in the frequency representation based on the modulus data. Data compression module 260 may store information relating to the N peaks, for example, in memory 220.

In one embodiment, N=100. Thus, one hundred (100) peaks in the frequency representation are selected.

In another embodiment, data compression module 260 sorts the 100 highest peaks based on their modulus, the magnitude and phase of the complex number.

In one embodiment, Equations (1) and (2) set forth below are used to determine N peaks in the frequency representation.

$$X_c(0) = \frac{1}{\sqrt{N}} \sum_{n=0}^{N-1} x(n) \tag{1}$$

$$X_c(k) = \sqrt{\frac{2}{N}} \sum_{n=0}^{N-1} x(n) \cos \frac{(2n+1)k\pi}{2N}, k = 1, 2, \ldots, (N-1) \tag{2}$$

At step 750, the first device transmits, to a second device, peaks information representing the N peaks. Thus, transceiver 230 of sensor device 100 transmits to data manager 435 data representing the N peaks in the frequency representation.

In accordance with an embodiment, the compressed data containing selected data from the frequency representation is received by a second device, and the second device generates a reconstructed version of the vibration data based on the compressed data.

Figure 8:
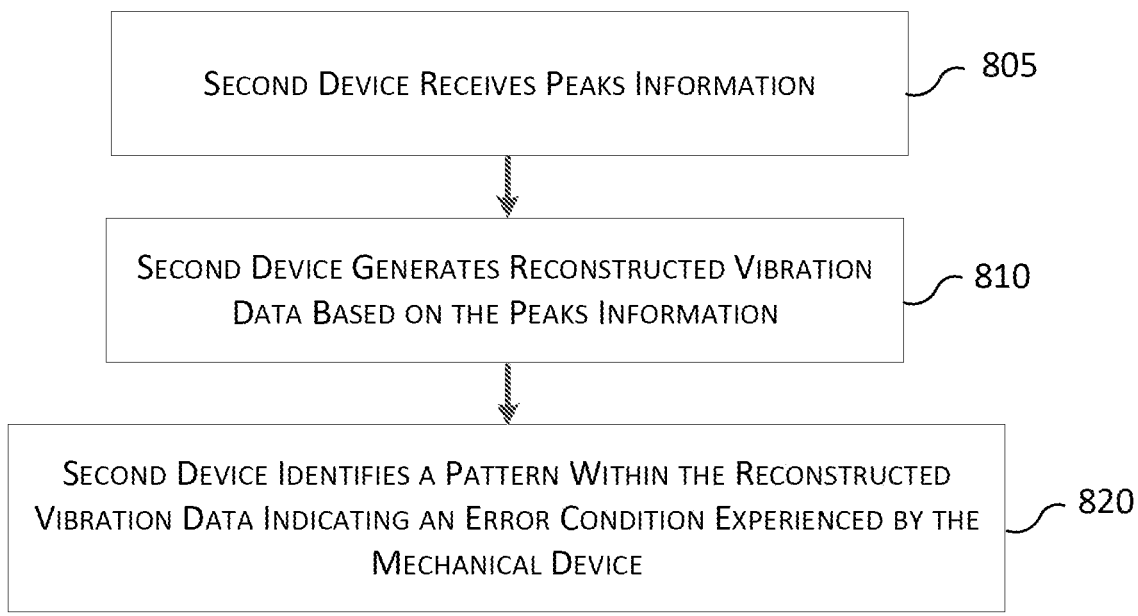
FIG. 8 is a flowchart of a method of receiving and analyzing data representing vibration data in accordance with an embodiment.

FIG. 8 is a flowchart of a method in accordance with an embodiment. At step 805, the second device receives the peaks information. In the illustrative embodiment, data manager 435 receives the peaks information transmitted by sensor device 100.

At step 810, the second device generates reconstructed vibration data based on the peaks information. After data manager 435 receives the peaks information representing the N peaks, data manager 435 causes vibration data reconstruction module 525 to generate reconstructed vibration data based on the peaks information. Data manager 435 stores the reconstructed vibration data in storage 530 as reconstructed vibration data 547.

At step 820, the second device identifies a pattern within the reconstructed vibration data indicating an error condition experienced by the mechanical machine. Fingerprint detection machine learning model 550 is applied to reconstructed vibration data 547 and identifies a pattern associated with an error condition.

Figure 9A:
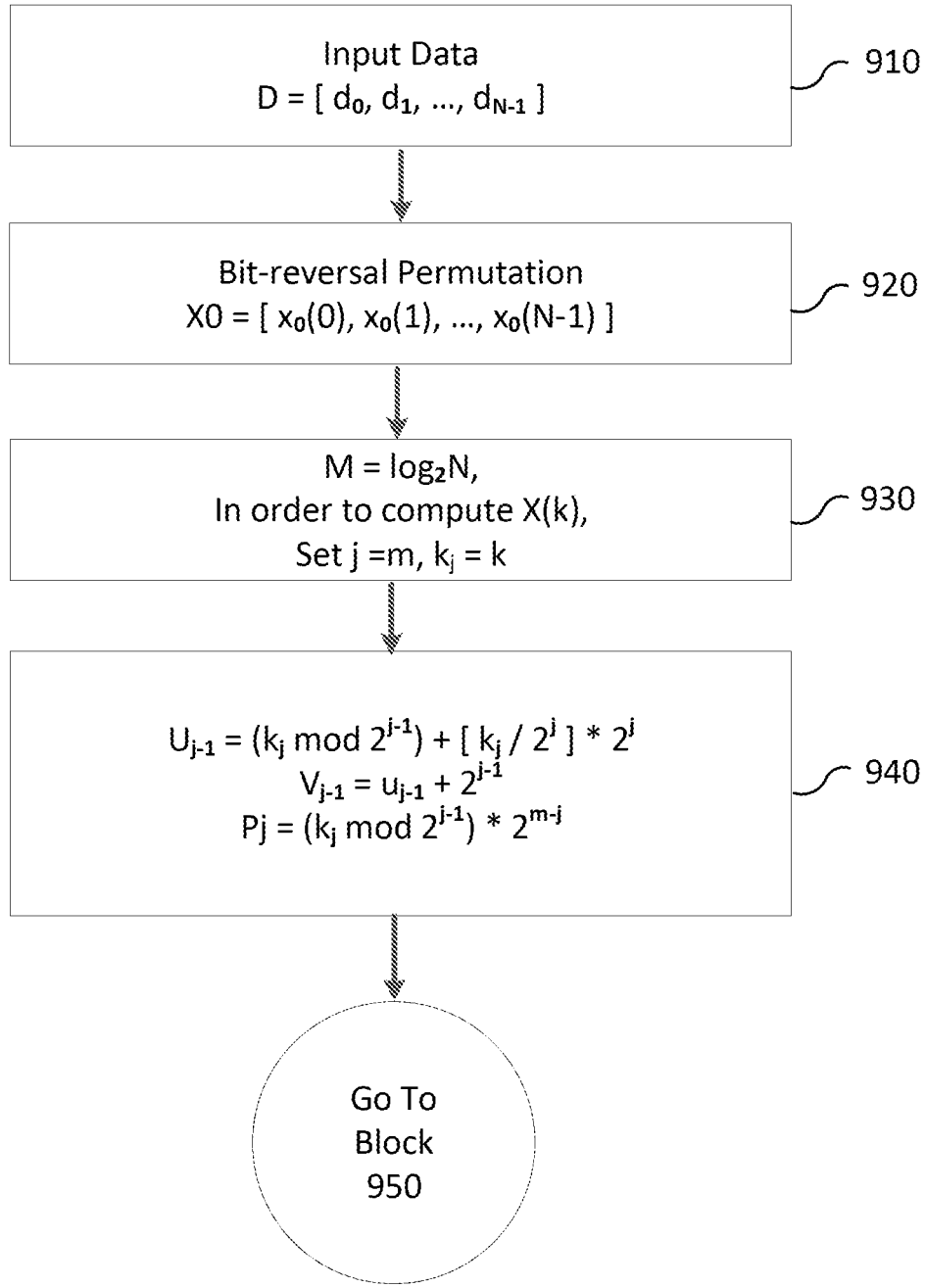
FIGS. 9A-9B include a flowchart of a method of using a modified Discrete Fourier Transform to generate a frequency representation of vibration data in accordance with an embodiment.
Figure 9B:
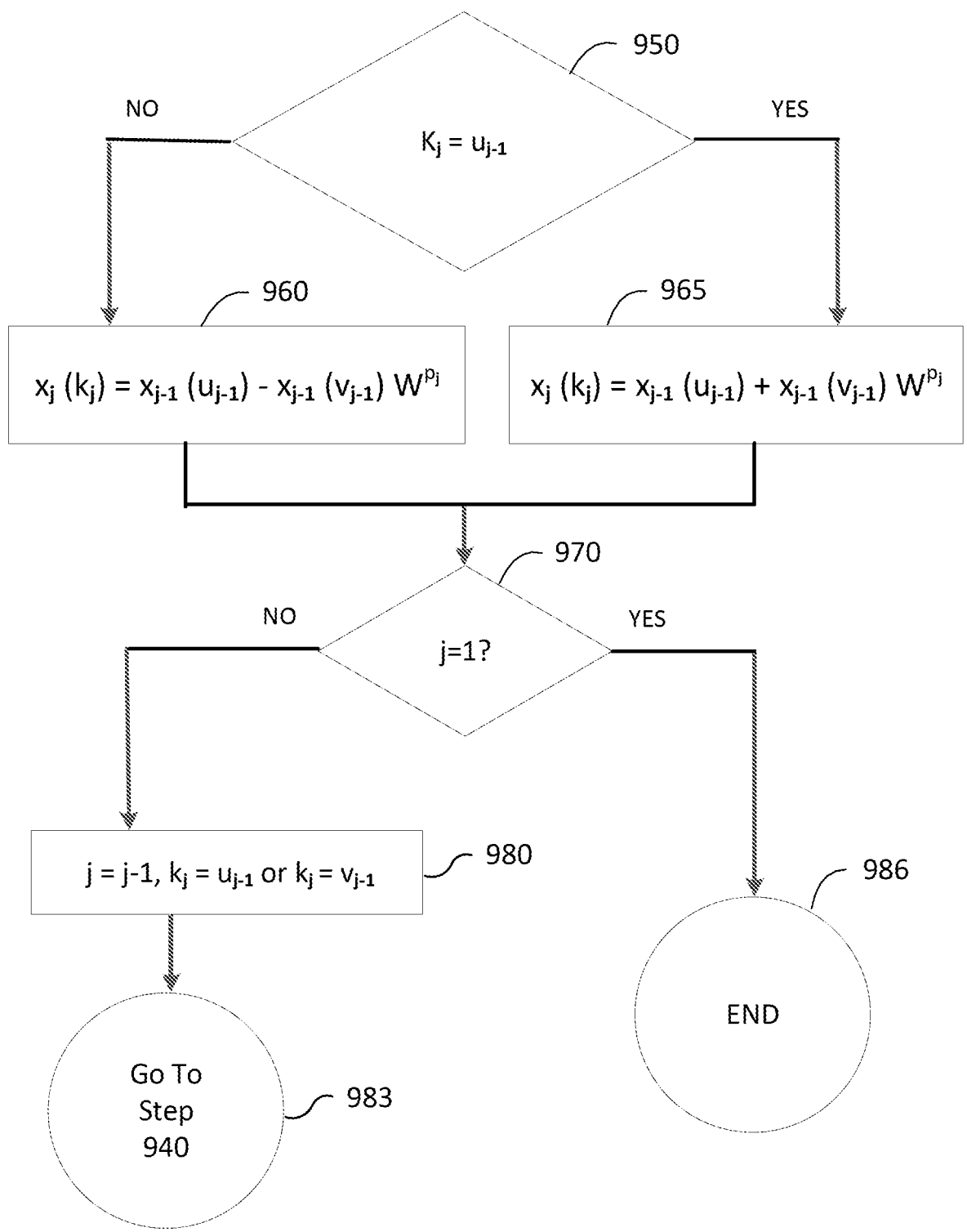

In various embodiments, any suitable method may be used to generate a frequency representation of the vibration data. In the illustrative embodiment, data compression module 260 of sensor 100 applies a modified Discrete Fourier Transform, using Fast Fourier Transform, to generate a frequency representation of the vibration data. FIGS. 9A-9B include a flowchart of a method of using a modified Discrete Fourier Transform to generate a frequency representation of vibration data in accordance with an embodiment.

At step 910, the vibration points are sampled and the sampled data is stored. In the illustrative embodiment, sensor device 100 uses processor 210 to sample the vibration points in time, and stores the sampled data in memory 220 for application of the custom discrete fourier transform algorithm.

At step 920, the sampled data undergoes a bit-reverse permutation process in which the input vector indices are inverted in a process with involution properties. In the illustrative embodiment, supposing an input of sampled N points (obtained in step 910), where N=$2^m$, the sampled points undergo a bit-reverse permutation process in which the input vector indices are inverted in a process with involution properties. The inversion process described consists of transforming an index 000 into 111 (or 010 into 101).

At step 930, the value of X(k) is obtained by defining the values of j and k, where j receives the value of m and $k_j$ receives the value of k. The method proceeds to step 940 with these values in the first iteration.

At step 940, $p_j$ is determined using the values of $u_{j-1}$ and $v_{j-1}$. In the notation used, the * operator indicates a rounding down to the nearest integer. To proceed, the recursive process performs steps 950, 960, 965, 970, 980 and 983 until j is equal to 1 in the check described in step 970.

After a series of recursive calls, the value of $x_0$ is found and then, using $x_0$, the value of $x_1$ is found, then $x_1$ is used to find $x_2$, and so on down to $x_m$. Finally, the value of X(k) is found through the sequence of recursive returns.

At step 940, the values of $u_{j-1}$ and $v_{j-1}$ are determined and used to obtain $p_j$.

At step 950, if $k_j$ has the same value as $u_{j-1}$, the method proceeds to step 965; otherwise, the routine proceeds to step 960.

At steps 965 and 960, the value of $x_j$ is obtained following the recursive logic. If j is equal to 1, the value in question is returned and the value of $x_0$ is obtained and by recursion $x_1$, $x_2, x_3, \ldots, x_m$.

At step 970, if j is different from 1, the values of j are updated to j−1 and $k_j$ to $u_{j-1}$ or $k_j$ to $v_{j-1}$ and the method returns to step 940 by the recursion process.

In accordance with another embodiment, a sensor samples vibration data, generates compressed vibration data, and transmits the compressed vibration data to data manager 435. Data manager 435 processes the compressed vibration data to generate reconstructed vibration data. Data manager 435 instructs the sensor to adjust parameters such as the sampling rate or sampling schedule in order to optimize the sensor's performance.

Figure 10A:
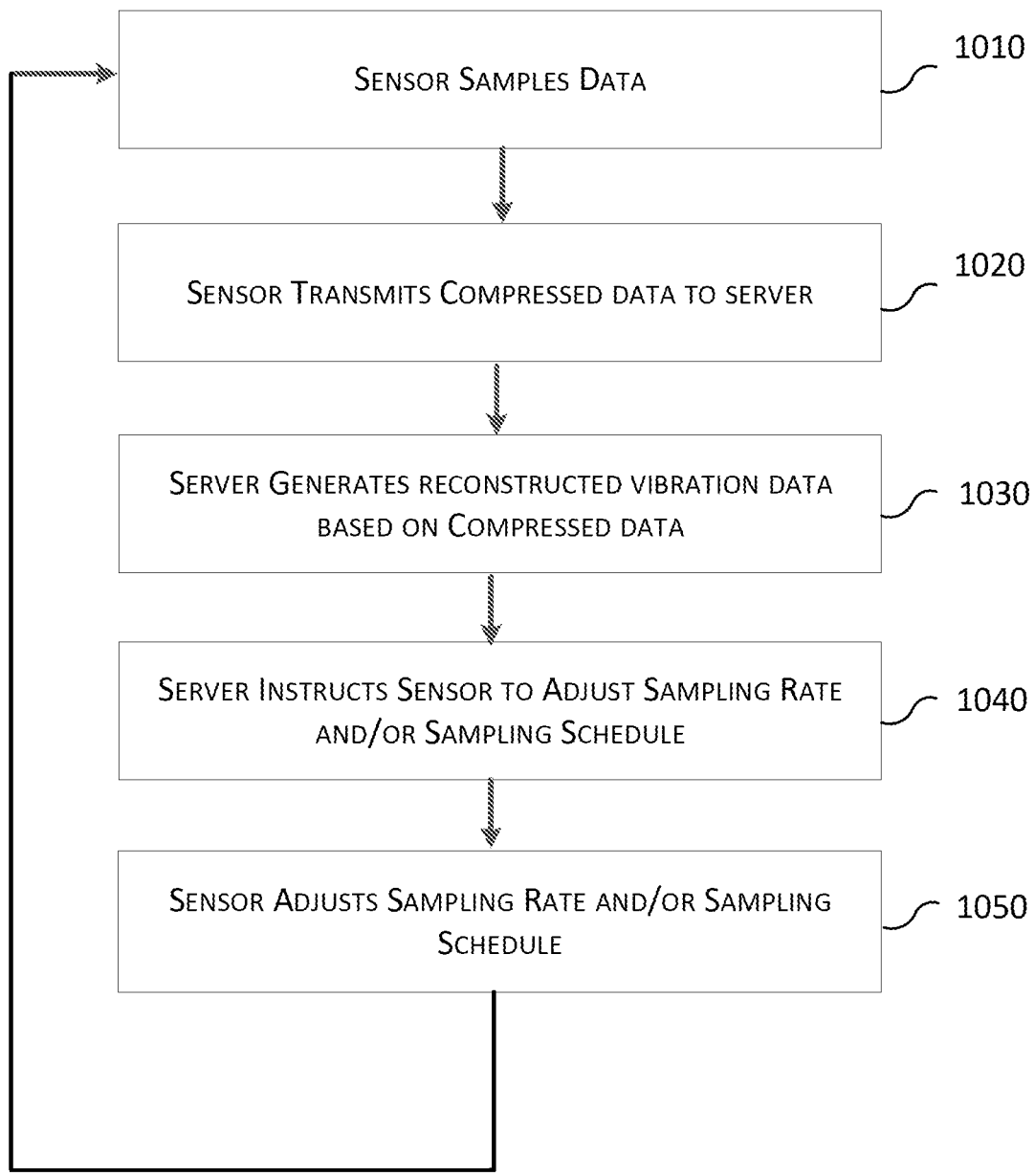
FIG. 10A is a flowchart of a method of obtaining, processing, and analyzing vibration data in accordance with an embodiment.

FIG. 10A is a flowchart of a method in accordance with an embodiment. At step 1010, the sensor samples data. In the illustrative embodiment, sensor device 100 samples vibration data generated by machine 50.

At step 1020, the sensor transmits compressed data to the server. In the illustrative embodiment, sensor device 100 compresses the vibration data and transmits the compressed vibration data to data manager 435. For example, sensor device 100 may generate a frequency representation of the vibration data, generate a reduced data set based on the frequency representation, and transmit the reduced data set to data manager 435.

At step 1030, the server generates reconstructed vibration data based on the compressed data. In the illustrative embodiment, data manager 435 generates reconstructed vibration data based on the compressed data received from sensor device 100. The reconstructed vibration data representing vibrations produced by machine 50.

At step 1040, the server instructs the sensor to adjust the sampling rate and/or the sampling schedule. At step 1050, the sensor adjusts the sampling rate and/or the sampling schedule. In the illustrative embodiment, data manager 435 identifies one or more adjustments to the sensor's sampling rate and/or sampling schedule that may increase the sensors performance, efficiency, etc., or optimize the collection of vibration data. Data manager 435 may make such a determination based on characteristics of machine 50 or based on the machine's pattern of operation. For example, some compressors (and other machines) operate according to a wake/sleep schedule and alternate between periods of operation (wake mode) and periods of inactivity (sleep mode); such machines must be sampled during the machine's wake mode. Thus, data manager 435 may instruct sensor device 100 to sample the vibration data only during the machine's wake modes. Alternatively, data manager 435 may determine that sensor device 100 should increase or decrease the sampling rate to obtain more data, to reduce the collection of redundant data, or for another reason. Other examples of adjustments that may be made include: sample more; sample less; change accelerometer parameters (e.g., 6.6 khz to 3.3 khz); sample above a vibration threshold (in case of 24/7 motors); increase or decrease tolerance; increasing the assertiveness overtime, etc.

Sensor device 100 adjusts the sampling rate and/or sampling schedule in accordance with the instructions received from data manager 435. The routine then returns to step 1010 and the sensor continues to sample data.

Figure 10B:
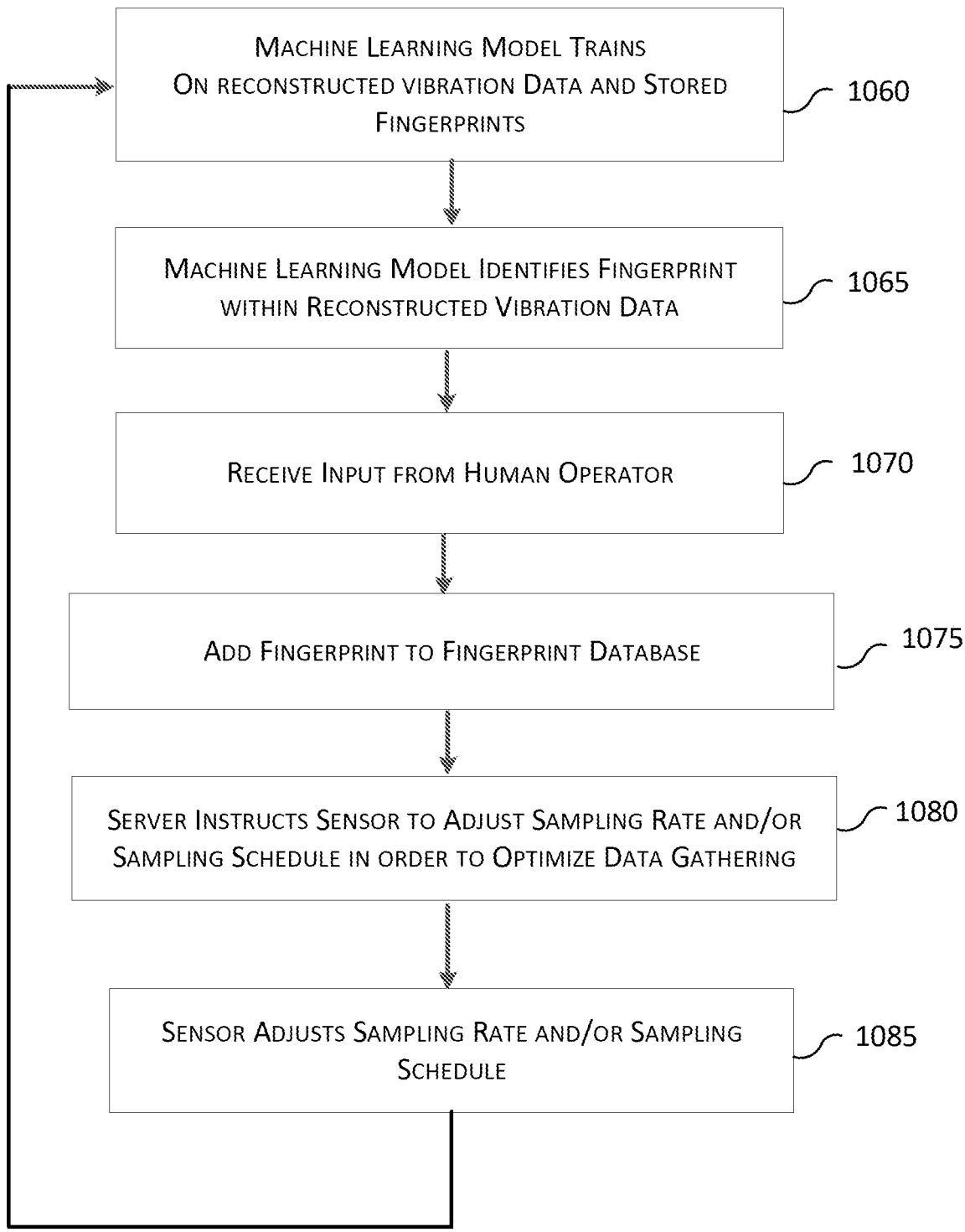
FIG. 10B is a flowchart of a method of analyzing vibration data in accordance with an embodiment.

In accordance with another embodiment, a machine learning model is applied to the data obtained by the sensor and identifies adjustments that the sensor may make to optimize the collection of vibration data. FIG. 10B is a flowchart of a method in accordance with an embodiment. The method of FIG. 10B and the method of FIG. 10A may be performed simultaneously.

At step 1060, the machine learning model trains on the reconstructed vibration data and on stored fingerprint data. In the illustrative embodiment, fingerprint detection machine learning model 550 trains on the reconstructed vibration data and the stored fingerprints in fingerprint database 545.

At step 1065, the machine learning model identifies a fingerprint within the reconstructed vibration data. Fingerprint detection machine learning model 550 identifies within the reconstructed vibration data a fingerprint associated with machine 50.

At step 1070, input is received from a human operator. For example, if data manager 435 identifies a fingerprint associated with an error condition, then a human operator may confirm that an error condition has occurred. In other embodiments, input from a human operator is not received. For example, if a fingerprint identifying a machine's normal mode of operation is identified, then no input from a human operator may be received.

At step 1075, the fingerprint is added to the fingerprint database. Data manager 435 stores the fingerprint in fingerprint database 545.

At step 1080, the server instructs the sensor to adjust the sampling rate and/or the sampling schedule in order to optimize data gathering. In the illustrative embodiment, fingerprint detection machine learning model 550 may identify adjustments that sensor device 100 should make in order to increase efficiency, bandwidth consumption, decrease false-positives, etc. Examples of adjustments that may be made include: sample more; sample less; change accelerometer parameters (e.g., 6.6 khz to 3.3 khz); sample above a vibration threshold (in case of 24/7 motors); increase or decrease tolerance; increasing the assertiveness overtime, etc. Data manager 435 instructs sensor device 100 to make adjustments accordingly.

At step 1085, the sensor adjusts the sampling rate and/or the sampling schedule in accordance with the instructions received. Sensor device 100 makes adjustments in accordance with the instructions received from data manager 435.

The routine then returns to step 1060 and the machine learning model continues to train on the sampled data and the (updated) fingerprint database.

Figure 11:
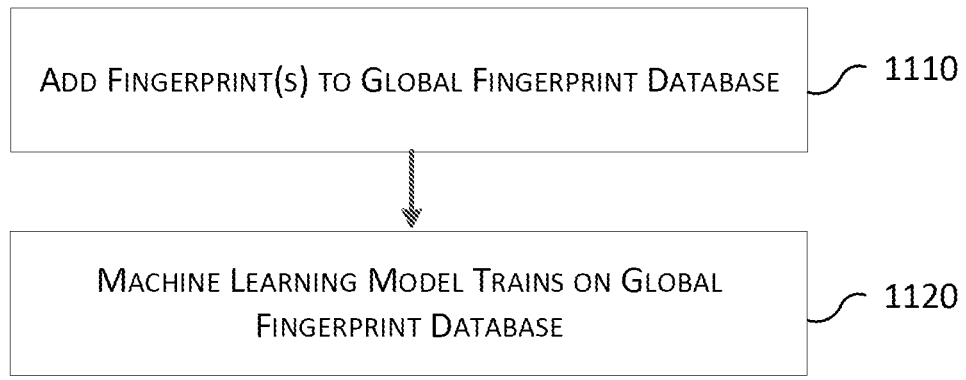
FIG. 11 is a flowchart of a method in accordance with an embodiment.

FIG. 11 is a flowchart of a method in accordance with an embodiment. The method of FIG. 11 and the methods of FIGS. 10A and 10B may be performed simultaneously.

At step 1110, a fingerprint is added to the global fingerprint database. Referring to FIG. 4, when a fingerprint is identified, data manager 435 stores the fingerprint in global fingerprint database 462 (in storage 460).

At step 1120, the machine learning model trains on the global fingerprint database. Thus, fingerprint detection machine learning model 550 trains on the fingerprints stored in global fingerprint database 462.

Advantageously, in one embodiment, the minimum assertiveness rate of the system, because of the global fingerprint database, has a 75% guaranteed positive error condition alerts.

In accordance with an embodiment, global fingerprint database 462 stores fingerprints associated with a variety of different machines. Machines, and the associated fingerprints, may be categorized into groups having similar characteristics. For example, categories may include machines having similar RPM, similar horsepower and foundation, etc.

In one embodiment, global fingerprint database 460 may include data similar to that shown in FIG. 12. FIG. 12 shows a table that contains exemplary characteristics associated with various types of machines in accordance with an embodiment. Specifically, table 1225 includes data associated with a centrifugal pump, a reciprocating pump, an electric motor, etc. The data stored in table 1225 may be used to define a fingerprint associated with a particular category of machine.

Accordingly, in the illustrative embodiment, fingerprint detection machine learning model 550 trains on data stored in global fingerprint database 462 that pertains to a category of machines relevant to machine 50, and learns patterns (e.g., the multiples of harmonics in the spectrum) that are associated with error conditions.

Thus, fingerprint detection machine learning model 550 may be trained on the data stored in global fingerprint database 462 and consequently learns fingerprints associated with machines that are similar to machine 50. Subsequently, when fingerprint detection machine learning model 550 is applied to reconstructed vibration data associated with machine 50, fingerprint detection machine learning model 550 may identify a fingerprint in the data based on its knowledge of the fingerprints of similar machines.

In one embodiment, in order to update global fingerprint database 460, data concerning each machine may be obtained from the user. For example, when a machine is installed, the following information may be collected from the user and stored in global fingerprint database 460: machine type (e.g., motor, pump, compressor, reductor, etc.), machine power (e.g., 15 KW, 30 KW, 0.5 KW, etc.), machine foundation (e.g., flexible, solid, shock absorber, cushion, etc.), maximum operating temperature (e.g., 30° C., 50° C., 80° C., etc.), machine bearing, rolling element diameter, outside track diameter, inner track diameter, machine fan/vane pass, measuring axis orientation (e.g., horizontal, vertical, axial, etc.). Other information may be obtained.

In various embodiments, the method steps described herein, including the method steps described in FIGS. 6A-6B, 10A-10B, and/or 11, may be performed in an order different from the particular order described or shown. In other embodiments, other steps may be provided, or steps may be eliminated, from the described methods.

Systems, apparatus, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be used within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc.

Systems, apparatus, and methods described herein may be implemented using a computer program product tangibly embodied in an information carrier, e.g., in a non-transitory machine-readable storage device, for execution by a programmable processor; and the method steps described herein, including one or more of the steps of FIGS. 6A-6B, 10A-10B, and/or 11, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 13:
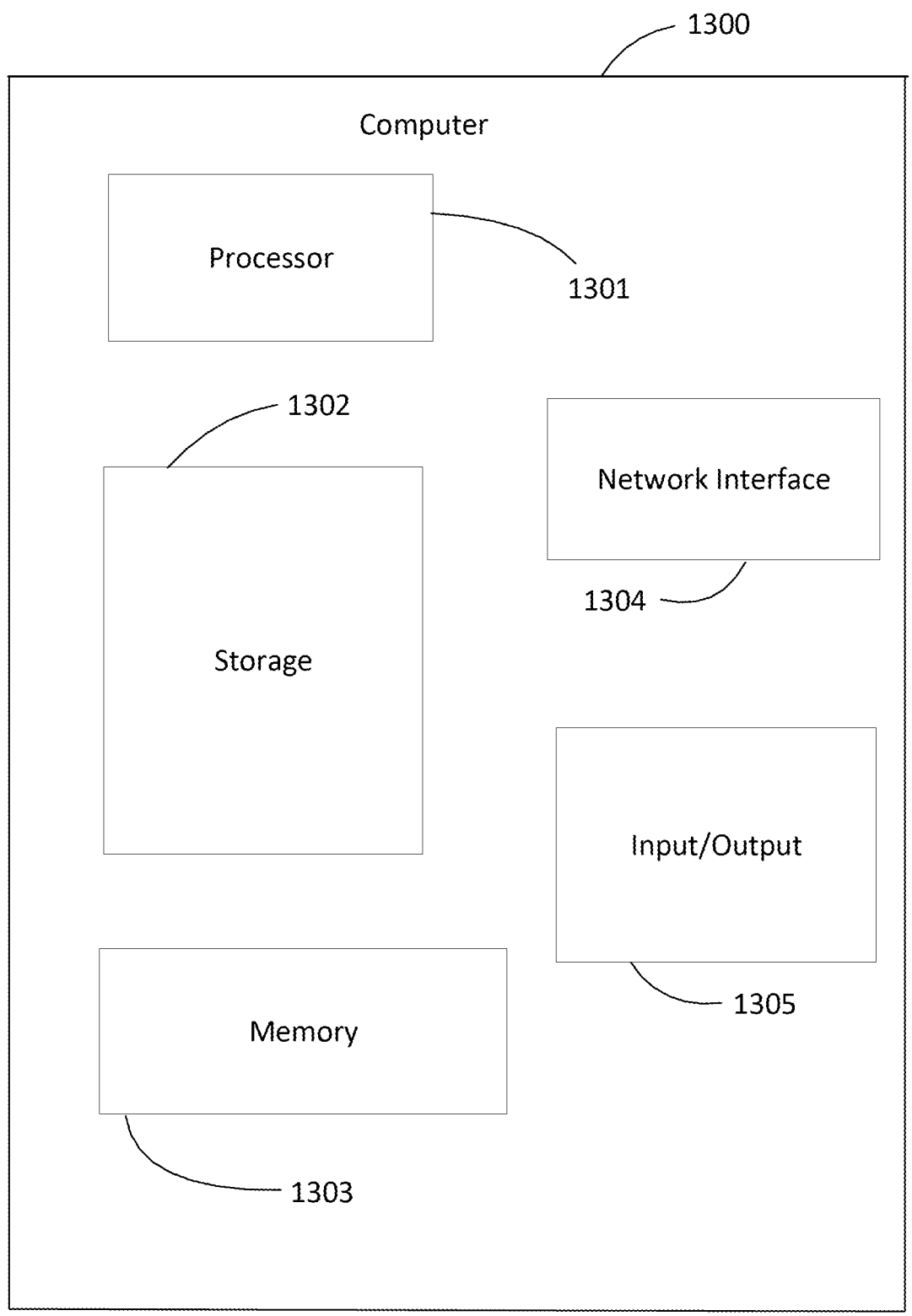
FIG. 13 shows components of an exemplary computer in accordance with an embodiment.

A high-level block diagram of an exemplary computer that may be used to implement systems, apparatus and methods described herein is illustrated in FIG. 13. Computer 1300 includes a processor 1301 operatively coupled to a data storage device 1302 and a memory 1303. Processor 1301 controls the overall operation of computer 1300 by executing computer program instructions that define such operations. The computer program instructions may be stored in data storage device 1302, or other computer readable medium, and loaded into memory 1303 when execution of the computer program instructions is desired. Thus, the method steps of FIGS. 6A-6B, 10A-10B, and/or 11, can be defined by the computer program instructions stored in memory 1303 and/or data storage device 1302 and controlled by the processor 1301 executing the computer program instructions. For example, the computer program instructions can be implemented as computer executable code programmed by one skilled in the art to perform an algorithm defined by the method steps of FIGS. 6A-6B, 10A-10B, and/or 11. Accordingly, by executing the computer program instructions, the processor 1301 executes an algorithm defined by the method steps of FIGS. 6A-6B, 10A-10B, and/or 11. Computer 1300 also includes one or more network interfaces 1304 for communicating with other devices via a network. Computer 1300 also includes one or more input/output devices 1305 that enable user interaction with computer 1300 (e.g., display, keyboard, mouse, speakers, buttons, etc.).

Processor 1301 may include both general and special purpose microprocessors, and may be the sole processor or one of multiple processors of computer 1300. Processor 1301 may include one or more central processing units (CPUs), for example. Processor 1301, data storage device 1302, and/or memory 1303 may include, be supplemented by, or incorporated in, one or more application-specific integrated circuits (ASICs) and/or one or more field programmable gate arrays (FPGAs).

Data storage device 1302 and memory 1303 each include a tangible non-transitory computer readable storage medium. Data storage device 1302, and memory 1303, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 1305 may include peripherals, such as a printer, scanner, display screen, etc. For example, input/output devices 1305 may include a display device such as a cathode ray tube (CRT) or liquid crystal display (LCD) monitor for displaying information to the user, a keyboard, and a pointing device such as a mouse or a trackball by which the user can provide input to computer 1300.

Any or all of the systems and apparatus discussed herein, including components thereof, may be implemented using a computer such as computer 1300.

One skilled in the art will recognize that an implementation of an actual computer or computer system may have other structures and may contain other components as well, and that FIG. 13 is a high-level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method comprising:
obtaining, by a first device, vibration data representing vibrations generated by a mechanical machine;
generating, by the first device, a frequency representation of the vibration data in a frequency spectrum, wherein generating the frequency representation comprises using a modified Discrete Fourier Transform, using Fast Fourier Transform, wherein the frequency representation includes a plurality of points defined by respective coefficients;
determining, by the first device, for each of the plurality of points in the frequency representation, a modulus of a magnitude and phase of the respective point, to generate modulus data;
selecting, by the first device, a predetermined number of peaks in the frequency representation based on the modulus data;
transmitting, by the first device, to a second device, peaks information representing the selected number of peaks;
training, by the second device, a machine learning model on first stored data that includes a plurality of samples of sampled vibration data associated with one or more mechanical machines different from the mechanical machine;
generating, by the second device, based on the peaks information, reconstructed vibration data representing the vibration data;
applying, by the second device, the machine learning model to the reconstructed vibration data;
identifying, by the machine learning model, a pattern within the reconstructed vibration data indicating an error condition experienced by the mechanical machine;
alerting, by the second device, a human operator that the pattern has been identified;
receiving, by the second device, from the human operator, a confirmation that the error condition exists;
adding the pattern to the first stored data, thereby generating second stored data, in response to receiving the confirmation from the human operator;
training, by the second device, the machine learning model on the second stored data;
determining, by the second device, based on the reconstructed vibration data, a schedule of operation of the mechanical machine, wherein the schedule includes a first period of operation and a second period of inactivity; and
instructing, by the second device, the first device to sample the vibrations only during the first period.

2. The method of claim 1, wherein the first device includes a sensor and is disposed on the mechanical machine.

3. The method of claim 1, wherein the mechanical machine is one of a compressor, a motor, a turbine, a pump, a bearing, a reductor, a fan, and a gearbox.

4. The method of claim 1, further comprising:
selecting, by the first device, one hundred (100) peaks in the frequency representation based on the modulus data.

5. The method of claim 1, wherein the error condition includes one of: a blockage, a cavitation, corrosion, an imbalance, a lubrification, a resonance, a rotating looseness, a deposit, a structural looseness, an operator error, and a transmitted fault.

6. A system comprising:
a first device comprising:
a sensor adapted to obtain vibration data representing vibrations generated by a mechanical machine;
a processor adapted to:
generate a frequency representation of the vibration data in a frequency spectrum, by using a modified Discrete Fourier Transform, using Fast Fourier Transform, wherein the frequency representation includes a plurality of points defined by respective coefficients;
determine, for each of the plurality of points in the frequency representation, a modulus of a magnitude and phase of the respective point, to generate modulus data;
select a predetermined number of peaks in the frequency representation based on the modulus data; and
a transmitting device adapted to transmit, to a second device, peaks information representing the selected number of peaks; and
a second device adapted to:
train a machine learning model on stored data that includes a plurality of samples of sampled vibration data associated with one or more mechanical machines;
generate, based on the peaks information, reconstructed vibration data representing the vibration data;
apply the machine learning model to the reconstructed vibration data;
identify a pattern within the reconstructed vibration data indicating an error condition experienced by the mechanical machine;
alert a human operator that the pattern has been identified;
receive, from the human operator, a confirmation that the error condition exists;
add the pattern to the first stored data, thereby generating second stored data, in response to receiving the confirmation from the human operator;
train the machine learning model on the second stored data;
determine, based on the reconstructed vibration data, a schedule of operation of the mechanical machine, wherein the schedule includes a first period of operation and a second period of inactivity; and
instruct the first device to sample the vibrations only during the first period.

7. The system of claim 6, wherein the first device is disposed on the mechanical machine.

8. The system of claim 6, wherein the mechanical machine is one of a compressor, a motor, a turbine, a pump, a bearing, a reductor, a fan, and a gearbox.

9. The system of claim 6, wherein the processor of the first device is further adapted to:
select one hundred (100) peaks in the frequency representation based on the modulus data.

10. The system of claim 6, wherein the error condition includes one of: a blockage, a cavitation, corrosion, an imbalance, a lubrification, a resonance, a rotating looseness, a deposit, a structural looseness, an operator error, and a transmitted fault.

* * * * *